(12) United States Patent
Bavouzet et al.

(10) Patent No.: US 7,846,423 B2
(45) Date of Patent: *Dec. 7, 2010

(54) COSMETIC COMPOSITION COMPRISING A BLOCK COPOLYMER

(75) Inventors: Bruno Bavouzet, Paris (FR); Mathias Destarac, Paris (FR); Pascal Herve, West Windsor, NJ (US); Agnieszka Zofia Wilczewska, Bialystok (PL)

(73) Assignee: Rhodia Chimie, Billancourt Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/803,064

(22) Filed: May 11, 2007

(65) Prior Publication Data

US 2007/0212322 A1  Sep. 13, 2007

Related U.S. Application Data

(62) Division of application No. 10/317,810, filed on Dec. 12, 2002, now Pat. No. 7,235,231.

(60) Provisional application No. 60/340,375, filed on Dec. 12, 2001.

(51) Int. Cl.
*A61Q 5/02* (2006.01)
*A61Q 19/00* (2006.01)

(52) U.S. Cl. .................. 424/70.11; 424/401; 424/70.15; 424/70.16; 424/70.17

(58) Field of Classification Search ....................... None
See application file for complete search history.

(56) References Cited

U.S. PATENT DOCUMENTS

| | | | |
|---|---|---|---|
| 5,273,676 A | 12/1993 | Boeckh | 252/174.21 |
| 6,139,826 A | 10/2000 | Schraer | 424/70.16 |
| 6,410,005 B1 | 6/2002 | Galleguillos | 424/70.16 |
| 6,528,476 B1 | 3/2003 | Bodet | 510/476 |
| 6,559,233 B2 * | 5/2003 | Bavouzet et al. | 525/244 |
| 6,864,314 B1 | 3/2005 | Yeung | 525/91 |
| 7,235,231 B2 * | 6/2007 | Bavouzet et al. | 424/70.16 |
| 2003/0027871 A1 | 2/2003 | Bendejacq et al. | 516/77 |
| 2003/0059391 A1 | 3/2003 | L'Alloret | 424/70.11 |
| 2003/0059392 A1 | 3/2003 | L'Alloret | 424/70.11 |
| 2003/0147826 A1 | 8/2003 | Anthony | 424/70.11 |
| 2004/0223933 A1 | 11/2004 | Hiwatashi | 424/70.11 |

FOREIGN PATENT DOCUMENTS

WO    WO-00/71591    11/2000

* cited by examiner

*Primary Examiner*—Jyothsna A Venkat
(74) *Attorney, Agent, or Firm*—Hunton & Williams LLP

(57) ABSTRACT

The present invention relates to a cosmetic composition comprising at least one diblock copolymer, as well as to the use of the said diblock copolymer as a modifier of properties of cosmetic compositions, more preferably of compositions for the skin and/or the hair. The diblock copolymer comprises two blocks, block A and block B, wherein block A is a polycationic block and block B is a neutral block.

14 Claims, No Drawings

COSMETIC COMPOSITION COMPRISING A BLOCK COPOLYMER

CROSS REFERENCES TO RELATED APPLICATIONS

This application claims the priority under 35 U.S.C. 119 and/or 365 to 60/340,375 filed in the United States on Dec. 12, 2001.

This application is a division of U.S. application Ser. No. 10/317,810, filed on Dec. 12, 2002 now U.S. Pat. No. 7,235,231.

BACKGROUND OF THE INVENTION

The present invention relates to a cosmetic composition comprising at least one diblock copolymer, as well as to the use of the said diblock copolymer as a modifier of properties of cosmetic compositions, more preferably of compositions for the skin and/or the hair.

BRIEF SUMMARY OF THE INVENTION

The invention relates to a cosmetic composition comprising at least a diblock copolymer, comprising two blocks A and B, wherein
- block A is a polycationic block in the pH conditions of the composition,
- block B is a neutral block in the pH conditions of the composition, and
- block A and block B both comprise units deriving from alpha-ethylenically-unsaturated, preferably from mono-alpha-unsaturated, monomers.

A second aspect of the invention relates to the use of diblock copolymers in a cosmetic composition, said diblock copolymer comprising t two blocks A and B, wherein
- block A is a polycationic block in the pH conditions of the composition,
- block B is a neutral block in the pH conditions of the composition, and
- block A and block B both comprise units deriving from alpha-ethylenically-unsaturated, preferably from mono-alpha-unsaturated, monomers.

DETAILED DESCRIPTION OF THE INVENTION

Definitions

In the present specification, the molecular weight of a polymer, a copolymer, a moiety, a graft, a side-chain, a core, a branch, a block or a backbone refers to the weight-average molecular weight of said polymer, copolymer, moiety, graft, side-chain, core, branch, block or backbone. The weight-average molecular weight of the polymer or copolymer can be measured by gel permeation chromatography (GPC). In the present specification, the molecular weight of a graft, side-chain, core, branch, block or backbone refers to the molecular weight calculated from the amounts of monomers, polymers, initiators and/or transfer agents used to make the said graft, side-chain, core, branch, block or backbone. The one skilled in the art knows how to calculate these molecular weights. The ratios by weight between moieties refer to the ratios between the amounts of the compounds used to make said moieties, considering an extensive polymerization.

Typically, the molecular weight M of a block, graft, side-chain, branch, core or backbone is calculated according to the following formula:

$$M = \sum_i M_i * \frac{n_i}{n_{precursor}},$$

wherein $M_i$ is the molecular weight of a monomer i, $n_i$ is the number of moles of a monomer i, and $n_{precursor}$ is the number of moles of a compound the macromolecular chain of the block, graft, side-chain, branch, core or backbone will be linked to. Said compound may be a transfer agent or a transfer group, a previous block, or a graft or reactive side-chain. If it is a previous block, the number of moles may be considered as the number of moles of a compound the macromolecular chain of said previous block has been linked to, for example a transfer agent or a transfer group. It may be also obtained by a calculation from a measured value of the molecular weight of said previous block. If two blocks are simultaneously grown from a previous block, at both ends, the molecular weight calculated according to the above formula should be divided by two.

In the present specification, a unit deriving from a monomer is understood as a unit that may be directly obtained from the said monomer by polymerizing. Thus, a unit deriving from an ester of acrylic or methacrylic acid does not encompass a unit of formula —CH—CH(COOH)— or —CH—C(CH$_3$)(COOH)—, obtained for example by polymerizing an ester of acrylic or methacrylic acid and then hydrolyzing. But a unit deriving from acrylic acid or methacrylic acid encompasses for example a unit obtained by polymerizing a monomer and then reacting (for example hydrolyzing) to obtain units of formula —CH—CH(COOH)— or —CH—C(CH$_3$)(COOH)—.

Diblock Copolymer

The diblock copolymer comprises two different blocks, block A, and block B. The diblock copolymer is a linear block copolymer. By linear it is meant that the two blocks arrangement is linear. However, a block may be a block having a comb polymer structure, that is comprising repetitive units comprising a polymeric moiety (macromonomers).

A block is usually defined by repeating units it comprises. A block may be defined by naming a polymer, or by naming monomers it is derived from. In the present specification, a unit deriving from a monomer is understood as a unit that may be directly obtained from the said monomer by polymerizing. Thus, a unit deriving from an ester of acrylic or methacrylic acid does not encompass a unit of formula —CH—CH(COOH)— or —CH—C(CH$_3$)(COOH)—, obtained for example by polymerizing an ester of acrylic or methacrylic acid and then hydrolyzing. But a unit deriving from acrylic acid or methacrylic acid encompasses for example a unit obtained by polymerizing a monomer and then reacting (for example hydrolyzing) to obtain units of formula —CH—CH(COOH)— or —CH—C(CH$_3$)(COOH)—.

A block may be a copolymer, comprising several kind of repeating units, deriving form several monomers. Hence, block A and block B are different polymers, deriving from different monomers, but they may comprise some common repeating units (copolymers). Block A and Block B preferably do not comprise more than 50% of a common repeating unit (derived from the same monomer).

Block A is a polyanionic block in the pH conditions of the composition. That means that block A comprises cationic repetitive units whatever the pH, or that block A comprises repetitive units that may be neutral or cationic depending on the pH of the composition (the units are potentially cationic).

A unit that may be neutral cationic, depending on the pH of the composition, will be thereafter referred to as a cationic unit, or as a unit deriving from a cationic monomer, whatever it is in a neutral form or in a cationic form.

Some preferred cationic monomers comprise an ammonium group of formula —$NR_3^+$, wherein R, which is identical or different, represents a hydrogen atom, an alkyl group comprising 1 to 10 carbon atoms, or a benzyl group, optionally carrying a hydroxyl group, and comprise an anion (counterion). Examples of anions are halides such as chloride and bromides, sulphates, hydrosulphates, alkylsulphates (for example comprising 1 to 6 carbon atoms), phosphates, citrates, formates, and acetates.

Examples of cationic monomers include
aminoalkyl (meth)acrylates, aminoalkyl (meth)acrylamides, monomers, including particularly (meth)acrylates, and (meth)acrylamides derivatives, comprising at least one secondary, tertiary or quaternary amine function, or a heterocyclic group containing a nitrogen atom, vinylamine or ethylenimine;

diallyldialkyl ammonium salts;

their mixtures, their salts, and macromonomers deriving from therefrom.

Examples of cationic monomers include:
dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;

ethylenimine, vinylamine, 2-vinylpyridine, 4-vinylpyridine;

trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido (also called 2-(acryloxy)ethyltrimethylammonium, TMAEAMS) chloride, trimethylammonium ethyl (meth)acrylate (also called 2-(acryloxy)ethyltrimethylammonium, TMAEAMS) methyl sulphate, trimethyl ammonium propyl (meth)acrylamido chloride, vinylbenzyl trimethyl ammonium chloride, diallyldimethyl ammonium chloride, monomers having the following formula:

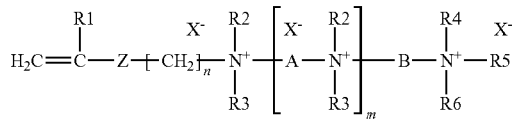

wherein $R_1$ is a hydrogen atom or a methyl or ethyl group;

$R_2$, $R_3$, $R_4$, $R_5$ and $R_6$, which are identical or different, are linear or branched $C_1$-$C_6$, preferably $C_1$-$C_4$, alkyl, hydroxyalkyl or aminoalkyl groups;

m is an integer from 1 to 10, for example 1;

n is an integer from 1 to 6, preferably 2 to 4;

Z represents a —C(O)O— or —C(O)NH— group or an oxygen atom;

A represents a $(CH_2)_p$ group, p being an integer from 1 to 6, preferably from 2 to 4;

B represents a linear or branched $C_2$-$C_{12}$, advantageously $C_3$-$C_6$, polymethylene chain optionally interrupted by one or more heteroatoms or heterogroups, in particular O or NH, and optionally substituted by one or more hydroxyl or amino groups, preferably hydroxyl groups;

X, which are identical or different, represent counterions, and their mixtures, and macromonomers deriving therefrom.

Block B is a neutral block in the pH conditions of the formulation. Units comprised in block B are preferably neutral whatever the pH.

Examples of neutral blocks are blocks comprising units deriving from at least one monomer selected from the group consisting of:

acrylamide, methacrylamide, amides of alpha-ethylenically-unsaturated, preferably mono-alpha-ethylenically-unsaturated, monocarboxylic acids, esters of an alpha-ethylenically-unsaturated, preferably mono-alpha-ethylenically-unsaturated, monocarboxylic acid, for example alkyl esters such as such as methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, or hydroxyalkyl esters such as 2-hydroxyethylacrylate, polyethylene and/or polypropylene oxide (meth)acrylates (i.e. polyethoxylated and/or polypropoxylated (meth)acrylic acid), vinyl alcohol, vinyl pyrrolidone, vinyl acetate, vinyl Versatate, vinyl nitriles, preferably comprising from 3 to 12 carbon atoms, acrylonitrile, vinylamine amides, vinyl aromatic compounds, such as styrene, and mixtures thereof.

Blocks that are ionic in the pH conditions of the formulation are usually considered as water-soluble. Thus, block A is usually considered as water-soluble. In a preferred embodiment of the invention, block B is water-soluble, or hydrophilic. Water-solubility of a block refers to the water-solubility that said block would have without the other block(s), that is the water-solubility of a polymer consisting of the same repeating units than said block, having the same molecular weight. By water-soluble block, polymer or copolymer, it is meant that the block, polymer or copolymer does not phase separate macroscopically in water at a concentration from 0.01% and 10% by weight, at a temperature from 20° C. to 30° C. By hydrophilic, it is meant that the moiety does not phase separate macroscopically in water at a concentration of from 0.1% and 1% by weight, at a temperature of from 20° C. to 30° C. By hydrophobic, it is meant that the moiety does phase separate macroscopically in water at a concentration of from 0.1% and 1% by weight, at a temperature of from 20° C. to 30° C.

As mentioned above, block B may be discriminated as regard to its hydrophilic or hydrophobic properties.

Examples of neutral blocks considered as hydrophilic include blocks comprising units deriving from at least one monomer selected from the group consisting of:

vinyl alcohol, vinyl pyrrolidone, acrylamide, methacrylamide, polyethylene oxide (meth)acrylate (i.e. polyethoxylated (meth)acrylic acid), hydroxyalkylesters of alpha-ethylenically-unsaturated, preferably mono-alpha-ethylenically-unsaturated, monocarboxylic acids, such as 2-hydroxyethylacrylate, and hdyroxyalkylamides of alpha-ethylenically-unsaturated, preferably mono-alpha-ethylenically-unsaturated, monocarboxylic acids.

Examples of neutral blocks considered as hydrophobic include blocks comprising units deriving from at least one monomer selected from the group consisting of:

alkylesters of an alpha-ethylenically-unsaturated, preferably mono-alpha-ethylenically-unsaturated, monocarboxylic acid, such as methylacrylate, ethylacrylate, n-propylacrylate, n-butylacrylate, methylmethacrylate, ethylmethacrylate, n-propylmethacrylate, n-butylmethacrylate, and 2-ethylhexyl acrylate, acrylonitrile vinyl nitriles, comprising from 3 to 12 carbon atoms, vinylamine amides, and vinylaromatic compounds such as styrene.

Both block A and block B derive from alpha-ethylenically-unsaturated, preferably mono-alpha-ethylenically-unsaturated, monomers. More precisely, it is meant that for block A and block B, at least 50% of the repeating units are alpha-ethylenically-unsaturated, preferably mono-alpha-ethylenically-unsaturated, monomers derived units. Examples of monomers mentioned above are alpha-ethylenically-unsaturated monomers.

From the monomers mentioned above, mono-alpha-ethylenically-unsaturated monomers include:

dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;

ethylenimine, vinylamine, 2-vinylpyridine, 4-vinylpyridine;

trimethylammonium ethyl (meth)acrylate (also called 2-(acryloxy)ethyltrimethylammonium, TMAEAMS) chloride, trimethylammonium ethyl (meth)acrylate (also called 2-(acryloxy)ethyltrimethylammonium, TMAEAMS) methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid 2-sulphoethyl methacrylate, salts of 2-sulphoethyl methacrylate, acrylamido-2-methylpropanesulphonic acid (AMPS), salts of acrylamido-2-methylpropanesulphonic acid, styrenesulfonate (SS), vinyl acetate, vinyl alcohol vinyl pyrrolidone, styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, and 2-hydroxyethylacrylate.

There are several methods for making copolymer (c) comprising moieties A and B. In a particular embodiment, copolymer (c) is a block copolymer or a star copolymer. Some methods for making such copolymers are provided below.

It is possible for example to use anionic polymerization with sequential addition of 2 monomers as described for example by Schmolka, J. Am. Oil Chem. Soc. 1977, 54, 110; or alternatively Wilczek-Veraet et al., Macromolecules 1996, 29, 4036. Another method which can be used consists in initiating the polymerization of a block polymer at each of the ends of another block polymer as described for example by Katayose and Kataoka, Proc. Intern. Symp. Control. Rel. Bioact. Materials, 1996, 23, 899.

In the context of the present invention, it is recommended to use living or controlled polymerization as defined by Quirk and Lee (Polymer International 27, 359 (1992)). Indeed, this particular method makes it possible to prepare polymers with a narrow dispersity and in which the length and the composition of the blocks are controlled by the stoichiometry and the degree of conversion. In the context of this type of polymerization, there are more particularly recommended the copolymers which can be obtained by any so-called living or controlled polymerization method such as, for example:

free-radical polymerization controlled by xanthates according to the teaching of Application WO 98/58974 and U.S. Pat. No. 6,153,705, free-radical polymerization controlled by dithioesters according to the teaching of Application WO 98/01478, free-radical polymerization controlled by dithioesters according to the teaching of Application WO 99/35178, free-radical polymerization controlled by dithiocarbamates according to the teaching of Application WO 99/35177, free-polymerization using nitroxide precursors according to the teaching of Application WO 99/03894, free-radical polymerization controlled by dithiocarbamates according to the teaching of Application WO 99/31144, free-radical polymerization controlled by dithiocarbazates according to the teaching of Application WO 02/26836, free-radical polymerization controlled by halogenated Xanthates according to the teaching of Application WO 00/75207 and U.S. application Ser. No. 09/980,387, free-radical polymerization controlled by dithiophosphoroesters according to the teaching of Application WO 02/10223, free-radical polymerization controlled by a transfer agent in the presence of a disulphur compound according to the teaching of Application WO 02/22688, atom transfer radical polymerization (ATRP) according to the teaching of Application WO 96/30421, free-radical polymerization controlled by iniferters according to the teaching of Otu et al., Makromol. Chem. Rapid. Commun., 3, 127 (1982), free-radical polymerization controlled by degenerative transfer of iodine according to the teaching of Tatemoto et al., Jap. 50, 127, 991 (1975), Daikin Kogyo Co Ltd Japan, and Matyjaszewski et al., Macromolecules, 28, 2093 (1995), group transfer polymerization according to the teaching of Webster O. W., "Group Transfer Polymerization", p. 580-588, in the "Encyclopedia of Polymer Science and Engineering", Vol. 7, edited by H. F. Mark, N. M. Bikales, C. G. Overberger and G. Menges, Wiley Interscience, New York, 1987, radical polymerization controlled by tetraphenylethane derivatives (D. Braun et al., Macromol. Symp., 111, 63 (1996)), radical polymerization controlled by organocobalt complexes (Wayland et al., J. Am. Chem. Soc., 116, 7973 (1994)).

Preferred processes are sequenced living free-radical polymerization processes, involving the use of a transfer agent. Preferred transfer agents are agents comprising a group of formula —S—C(S)—Y—, —S—C(S)—S—, or —S—P(S)—Y—, or —S—P(S)—S—, wherein Y is an atom different from sulfur, such as an oxygen atom, a nitrogen atom, and a carbon atom. They include dithioester groups, thioetherthione groups, dithiocarbamate groups, dithiphosphoroesters, dithiocarbazates, and xanthate groups. Examples of groups comprised in preferred transfer agents include groups of formula —S—C(S)—NR—NR'$_2$, —S—C(S)—NR—N=CR'$_2$, —S—C(S)—O—R, —S—C(S)—CR=CR'$_2$, and —S—C(S)—X, wherein R and R' are or identical or different hydrogen atoms, or organic groups such as hydrocarbyl groups, optionally substituted, optionally comprising heteroatoms, and X is an halogen atom. A preferred polymerization process is a living radical polymerization using xanthates.

Copolymers obtained by a living or controlled free-radical polymerization process may comprise at least one transfer agent group at an end of the polymer chain. In particular embodiment such a group is removed or deactivated.

A "living" or "controlled" radical polymerization process used to make the diblock copolymers comprises the steps of:

a) reacting a mono-alpha-ethylenically-unsaturated monomer, at least a free radicals source compound, and a transfer agent, to obtain a first block, the transfer agent being bounded to said first block, b) reacting the first block, another mono-alpha-ethylenically-unsaturated monomer, and, optionally, at least a radical source compound, to obtain a diblock copolymer, and then c) optionally, reacting the transfer agent with means to render it inactive.

During step a), a first block of the polymer is synthesized. During step b), the other block of the polymer is synthesized.

Examples of transfer agents are transfer agents of the following formula (I):

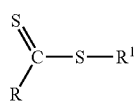
(I)

wherein:

R represents an R$^2$O—, R$^2$R'$^2$N— or R$^3$— group, R$^2$ and R'$^2$, which are identical or different, representing (i) an alkyl, acyl, aryl, alkene or alkyne group or (ii) an optionally aromatic, saturated or unsaturated carbonaceous ring or (iii) a saturated or unsaturated heterocycle, it being possible for these groups and rings (i), (ii) and (iii) to be substituted, R$^3$ representing H, Cl, an alkyl, aryl, alkene or alkyne group, an optionally substituted, saturated or unsaturated (hetero)cycle, an alkylthio, alkoxycarbonyl, aryloxycarbonyl, carboxyl, acyloxy, carbamoyl, cyano, dialkyl- or diarylphosphonato, or dialkyl- or diarylphosphinato group, or a polymer chain, R$^1$ represents (i) an optionally substituted alkyl, acyl, aryl, alkene or alkyne group or (ii) a carbonaceous ring which is saturated or unsaturated and which is optionally substituted or aromatic or (iii) an optionally substituted, saturated or unsaturated heterocycle or a polymer chain, and The R$^1$, R$^2$, R'$^2$ and R$^3$ groups can be substituted by substituted phenyl or alkyl groups, substituted aromatic groups or the following groups: oxo, alkoxycarbonyl or aryloxycarbonyl (—COOR), carboxyl (—COOH), acyloxy (—O$_2$CR), carbamoyl (—CONR$_2$), cyano (—CN), alkylcarbonyl, alkylarylcarbonyl, arylcarbonyl, arylalkylcarbonyl, isocyanato, phthalimido, maleimido, succinimido, amidino, guanidino, hydroxyl (—OH), amino (—NR$_2$), halogen, allyl, epoxy, alkoxy (—OR), S-alkyl, S-aryl or silyl, groups exhibiting a hydrophilic or ionic nature, such as alkaline salts of carboxylic acids or alkaline salts of sulphonic acid, poly(alkylene oxide) (PEO, PPO) chains, or cationic substituents (quaternary ammonium salts), R representing an alkyl or aryl group.

Preferably, the transfer agent of formula (I) is a dithiocarbonate chosen from the compounds of following formulae (IA), (IB) and (IC):

(IA)

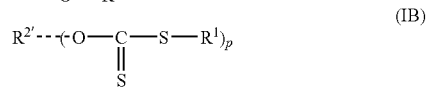
(IB)

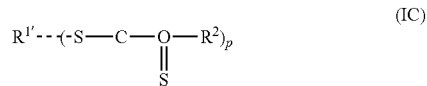
(IC)

wherein:

R$^2$ and R$^{2'}$ represent (i) an alkyl, acyl, aryl, alkene or alkyne group or (ii) an optionally aromatic, saturated or unsaturated carbonaceous ring or (iii) a saturated or unsaturated heterocycle, it being possible for these groups and rings (i), (ii) and (iii) to be substituted, R$^1$ and R$^{1'}$ represent (i) an optionally substituted alkyl, acyl, aryl, alkene or alkyne group or (ii) a carbonaceous ring which is saturated or unsaturated and which is optionally substituted or aromatic or (iii) an optionally substituted, saturated or unsaturated heterocycle or a polymer chain, and p is between 2 and 10.

Other examples of transfer agents are transfer agents of the following formulae (II) and (III):

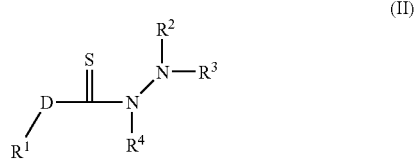
(II)

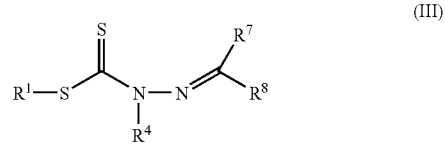
(III)

wherein $R^1$ is an organic group, for example a group $R^1$ as defined above for transfer agents of formulae (I), (IA), (IB), and (IC), $R^2$, $R^3$, $R^4$, $R^7$, and $R^8$ which are identical or different are hydrogen atoms or organic groups, optionally forming rings. Examples of $R^2$, $R^3$, $R^4$, $R^7$, and $R^8$ organic groups include hydrocarbyls, substituted hydrocarbyls, heteroatom-containing hydrocarbyls, and substituted heteroatom-containing hydrocarbyls.

The mono-alpha-ethylenically-unsaturated monomers and their proportions are chosen in order to obtain the desire properties for the block(s). According to this process, if all the successive polymerizations are carried out in the same reactor, it is generally preferable for all the monomers used during one stage to have been consumed before the polymerization of the following stage begins, therefore before the new monomers are introduced. However, it may happen that monomers of the preceding stage are still present in the reactor during the polymerization of the following block. In this case, these monomers generally do not represent more than 5 mol % of all the monomers.

The polymerization can be carried out in an aqueous and/or organic solvent medium. The polymerization can also be carried out in a substantially neat melted form (bulk polymerization), or according to a latex type process in an aqueous medium.

The molecular weight of block copolymer (c) is preferably comprised between 1000 and 500000 g/mol. It is more preferably less than 100000 g/mol, and further more preferably between 15000 and 20000 g/mol. Within these ranges, the weight ratio of each block may vary. It is however preferred that each block have a molecular weight above 500 g/mol, and preferably above 1000 g/mol.

Composition

The terms "cosmetic composition" and "cosmetic formulation" mean any cosmetic product or preparation of the type described in Annex I ("Illustrative list by category of cosmetic products") of European Directive No. 76/768/EEC of 27 Jul. 1976, known as the Cosmetics Directive.

The cosmetic compositions can be formulated in a large number of types of product for the skin and/or the hair such as mousses, gels (in particular styling gels), masks for the face or the hair, conditioners, formulations for improving hairstyling, or for facilitating the combing or disentangling of the hair, for providing volume or sheen, rinsing formulations, hand and body lotions and oils, products for improving the moisturization of the skin, cleansing milks, make-up-removing compositions, creams or lotions for protecting against the sun and ultraviolet radiation, care and/or treatment milks and creams, anti-acne preparations, local analgesics, mascaras, products intended to be applied to the lips or other mucous membranes, sticks, deodorant and antiperspirant products, shaving lotions, bath oils, talcs and other compositions of the same type.

Examples of compound comprised in a cosmetic composition according to the invention include surfactant, vehicles, emollients, and conditioning agents.

Examples of vehicles include water, alcohols such as ethanol and isopropanol, as well as other solvents such as hydrocarbons, halohydrocarbons, linalool, esters and volatile silicones. Vehicle compounds may be soluble which each other, or not. Other compounds of the cosmetic composition may be soluble in the vehicle, or not.

When the cosmetic compositions are in the form of sprays, tonic lotions, gels or mousses, the preferred vehicles comprise ethanol, volatile silicone derivatives or mixtures thereof.

The formulations for mousses and aerosol sprays can thus contain a propellant capable of generating the products in the form of mousses or fine uniform sprays. Examples which may be mentioned are dimethyl ether, propane, n-butane and isobutane.

Examples of surfactant include:
anionic surfactants, such as:
alkyl ester sulphonates,
alkyl sulphates,
alkylamide sulphates, and
saturated or unsaturated fatty acid salts,
nonionic surfactants, such as:
polyoxyalkylenated alkylphenols,
glucosamides, glucamides,
glycerolamides derived from N-alkylamines,
polyoxyalkylenated $C_8$-$C_{22}$ aliphatic alcohols,
the products resulting from the condensation of ethylene oxide with a hydrophobic compound resulting from the condensation of propylene oxide with propylene glycol,
amine oxides,
alkylpolyglycosides and polyoxyalkylenated derivatives thereof,
$C_8$-$C_{20}$ fatty acid amides,
ethoxylated fatty acids, and
ethoxylated amides, amines or amidoamines, and
amphoteric and zwitterionic surfactants, such as:
those of betain type, such as:
betaines,
sulpho-betaines,
amidoalkylbetaines, and
sulpho-betaines,
alkylsultaines
the products of condensation of fatty acids and of protein hydrolysates,
cocoamphoacetates and cocoamphodiacetates,
alkylampho-propionates or -dipropionates, and
amphoteric alkylpolyamine derivatives.

Examples of emollients include alkylmonoglycerides, alkyldiglycerides, triglycerides such as oils extracted from plants and vegetables (palm oil, coconut oil, cotton seed oil, soybean oil, sunflower oil, olive oil, grapeseed oil, sesame oil, ground nut oil, castor oil, argan oil, etc.) or oils of marine origin (fish oils, etc.), derivatives of these oils, such as hydrogenated oils, lanolin derivatives, mineral oils or paraffinic oils, perhydrosqualene, squalene, diols such as 1,2-propanediol and 1,3-butanediol, cetyl alcohol, stearyl alcohol, oleyl alcohol, polyethylene glycols or polypropylene glycols, fatty esters such as isopropyl palmitate, 2-ethylhexyl cocoate, myristyl myristate, esters of lactic acid, stearic acid, behenic acid, isostearic acid, silicone oils combining cyclic polydimethylsiloxanes, $\alpha,\omega$-hydroxylated polydimethylsiloxanes, $\alpha,\omega$-trimethylsilyl polydimethylsiloxanes, polyorganosiloxanes such as polyalkylmethylsiloxanes, polymethylphenylsiloxanes, polydiphenylsiloxanes, aminosilicone derivatives, silicone waxes, copolyether silicones (such as the oil Mirasil DMCO sold by the company Rhodia or DC 190 sold by Dow Corning) or mixed silicone derivatives including various types of derivatization (such as polyalkylmethyl-siloxane/copolyether silicone mixed copolymers).

Examples of conditioning agents include agents of natural or synthetic origin, such as those known under the generic CTFA name "Polyquaternium", for instance the Mirapol A15® or Mirapol 550® polymers from the company Rhodia, cationic polysaccharide derivatives (cationic derivatives of cellulose, of guar or of carob), such as cocodimonium hydroxyethyl cellulose, guar hydroxypropyl trimonium chloride, hydroxypropyl guar hydroxypropyl trimonium chloride (Jaguar C13S®, Jaguar C162® sold by Rhodia), volatile or non-volatile silicone derivatives, for instance amodimethicone, cyclomethicones, water-insoluble, non-volatile polyorganosiloxanes, for instance oils, resins or gums, such as diphenyldimethicone gums.

Various compounds which are useful for promoting moisturization of the skin (wetting agents) may also be comprised in the cosmetic compositions according to the invention. Examples of such compounds include certain carbohydrates (for example glycerol or sorbitol), polyethylene glycols or polypropylene glycols, alkoxylated derivatives of sugars or of sugar derivatives (for example methylglucose), water-soluble or water-dispersible polymers such as collagen or certain non-allergenic derivatives of marine or plant proteins (for example wheat protein hydrolysates).

Cosmetic compositions according to the invention may also comprise thickeners. Examples of thickeners include natural hydrocolloids (guar gum, carob gum, tara gum, etc.) or hydrocolloids derived from fermentation processes, such as xanthan gum, polysaccharides extracted from seaweed, such as carrageenans, and polycarbohydrate derivatives such as modified celluloses (for example hydroxyethylcellulose, carboxymethylcellulose), or nonionic derivatives (for example hydroxypropylguar), anionic derivatives (carboxymethylguar) or nonionic/anionic mixed derivatives, such as carboxy-hydroxypropyl-guars or nonionic/cationic derivatives.

Cosmetic compositions according to the invention may also comprise mineral powders or particles such as calcium carbonate, mineral oxides in powder form or in colloidal form (particles of the order of or smaller than one micrometer in size, occasionally a few tens of nanometers), such as titanium dioxide, silica, aluminium salts generally used as antiperspirants, kaolin, talc, clays and clay derivatives, etc., and any mineral pigment used in make-up formulations, can be added to these compounds in combination.

Cosmetic compositions according to the invention may also comprise preserving agents such as methyl, ethyl, propyl and butyl esters of p-hydroxybenzoic acid, sodium benzoate, DMDM hydantoin or any chemical agent which prevents the proliferation of bacteria or moulds and which is among the list of authorized and/or provisionally authorized preserving agents, mentioned in Annex VI of European Directive No. 76/78/EEC, conventionally used in cosmetic compositions are generally introduced into these compositions to a proportion of from 0.01 to 3% by weight. The amount of these products is generally adjusted to avoid any proliferation of bacteria, moulds or yeasts in the cosmetic compositions.

To protect the skin or the hair against attack from the sun and UV rays, cosmetic compositions according to the invention may comprise sunscreens, which are chemical compounds which absorb UV radiation strongly, for instance the compounds authorized in European Directive No. 76/768/EEC, its annexes and subsequent modifications, or titanium dioxide or cerium oxides in the form of powder or colloidal particles. These powders can optionally be surface-treated to increase the efficacy of their UV-stabilizing action or to facilitate their incorporation into cosmetic formulations or to inhibit the surface photoreactivity.

Cosmetic compositions according to the invention may also comprise fragrances, dyes or pigments, to make the composition more pleasant for the consumer to use.

Cosmetic compositions may also comprise resins for fixing to keratin support, in concentrations of between 0.5 and 10%, preferably between 1 and 5%. They are preferably selected from the group consisting of the following resins: methyl acrylate/acrylamide copolymers, polyvinyl methyl ether/maleic anhydride copolymers, vinyl acetate/crotonic acid copolymers, octylacrylamide/methyl acrylate/butylaminoethyl methacrylate copolymers, polyvinylpyrrolidones, polyvinylpyrrolidone/methyl methacrylate copolymers, polyvinylpyrrolidone/vinyl acetate copolymers, polyvinyl alcohols, polyvinyl alcohol/crotonic acid copolymers, polyvinyl alcohol/maleic anhydride copolymers, hydroxypropylcelluloses, hydroxypropylguars, sodium polystyrenesulphonates, polyvinylpyrrolidone/ethyl methacrylate/methacrylic acid terpolymers, poly(methyl vinyl ether/maleic acid)monomethyl ethers, polyethylene glycol terephthalate/polyethylene glycol copolymers, polyethylene glycol terephthalate/polyethylene glycol/poly(sodium isophthalate sulphonate) copolymers, sulphonated polyesters containing polyorganosiloxane units; cationic resins totally or partially derived from cationic monomers such as, for example, dimethylaminoethyl methacrylate, quaternized dimethylaminoethyl methacrylate, diallyldimethyl-ammonium chloride, and mixtures thereof. Cationic resins can also be based on water-soluble natural polymers such as, for example, cationic polysaccharides, for instance cationic guar or cationic cellulose, or mixtures thereof.

The diblock copolymer provides numerous benefits to cosmetic compositions. The use of said diblock copolymer as an additive in cosmetic compositions may modify properties of the cosmetic composition or address formulations issues relating to the different compounds that may be comprised in a cosmetic composition. By modifying properties, it is meant that one of the properties, or function of another compound, is enhanced (or decreased, if it is a problem). By addressing a formulation issue, it is meant that some incompatible compounds (or incompatible relative amounts of said compounds) are more compatible, allowing to optimize the performance and/or the aspect and/or the cost, and/or environment issues, and/or sensory properties, of the composition.

Without intending to be bound to any theory, it is believed that some benefits are due to the particular structure of the diblock copolymers: one block may interact with at least one of the compounds of the composition, the other block may interact with at least another compound and/or with skin or hair. For example, it is believed that cationic block A interacts compounds having an affinity with cationic compounds such as hair and/or skin. As a further example, block A interacts with an anionic surfactant. Block B interacts with other compounds, depending if it is hydrophilic or hydrophobic. Thus, adding the diblock copolymer allows modifying the formulation of a composition comprising an anionic surfactant, in order for example to lower the amount of the surfactant, which is cost-effective, and environment friendly.

Some examples of benefits of the use of the diblock copolymers according to the invention include:

Depositing a polymer onto hair and/or skin. Diblock copolymers deposit onto hair and/or skin, allowing for example a better web-combing, to providing the hair with a conditioning effect. Diblock copolymers also enhance or trigger the deposition of other compounds, such as silicone emulsions, or cationic conditioning polymers.

Avoiding phase separation of a suspension of colloids comprising an anionic copolymer and a cationic polymer.

Stabilizing emulsions (preferably oil in water emulsions, or triple emulsions). Benefits are not limited to the examples above.

EXAMPLES

Example 1

A cationic-neutral diblock copolymer is made up of a polyTMAEAMS (methylsulfate[2-(acryloyloxy)ethyl]-trimethylammonium) first block (Mw=11,000 g/mole) and a polyacrylamide second block (Mw=3,000 g/mole) noted polyTMAEAMS$_{11k}$-b-polyAM$_{3k}$.

1/ Synthesis of a Diblock Copolymer polyTMAEAMS-b-polyAM 11K-3K

The synthesis is carried out according to a batch process, at 70° C., in a double-jacketed reactor.

First Stage: polyTMAEAMS$_{11k}$-X Synthesis

The solution of [2-(acryloyloxy)ethyl]-trimethylammonium methyl sulfate (TMAEAMS) and water are introduced in the reactor and the solution is heated to 70° C. Then a mixture of S-ethylpropionyl O-ethyl xanthate, 4,4'-azo-bis-4-cyanovaleric acid or ACVA (30 mole % relative to the xanthate) and isopropanol is introduced. The obtained mixture is stirred overnight at 70° C.

| Mass of the reagents introduced per 100 g of final diblock solution | | | | |
|---|---|---|---|---|
| TMAEAMS (80 w % in water) | Water | Xanthate | ACVA | Isopropanol |
| 12.69 g | 16.92 g | 0.20 g | 0.08 g | 3.32 g |

Second Stage: polyTMAEAMS$_{11k}$-PAM$_{3k}$ Synthesis

The ACVA (50 mole % relative to the xanthate) dissolved in the water is added to the previous mixture.

| Mass of the reagents introduced | |
|---|---|
| ACVA | Water |
| 0.13 g | 49.86 g |

The acrylamide dissolved in the water (I) is then added continuously during 3 hours. After the first hour, the ACVA (22 mole % relative to the xanthate) dissolved in the water (II) is added.

| Mass of the reagents introduced | | | |
|---|---|---|---|
| Acrylamide | Water (I) | ACVA | Water (II) |
| 2.77 g | 7.87 g | 0.06 g | 3.00 g |

After the second hour, the ACVA (22 mole % relative to the xanthate) dissolved in the water is added.

| Mass of the reagents introduced | |
|---|---|
| ACVA | Water |
| 0.06 g | 3.00 g |

After the three hours, the mixture is again stirred at 70° C. for two hours.

The dry extract of the final solution is 13.2%.

Consequently a series of diblock copolymers polyTMAEAMS$_{11k}$-b-polyAM$_{xk}$ with (X=0, 3, 15 and 30) were synthesized according to the protocol described above adapting for each one of them to the adequate quantities of acrylamide, water, initiator and transfer agent.

The diblock copolymer is used in a hair-care composition. The composition provides improved wet combing.

Example 2

A cationic-neutral diblock copolymer is made up of a poly (butyl acrylate) first block (Mn=2,000 g/mole) and a poly([2-dimethylaminoethyl acrylate) (Mn=4,000 g/mole) noted polyABU$_{2k}$-b-polyADAM$_{4k}$.

The reactions are carried out in a 1 liter reactor comprising refrigerating means, a magnetic stirrer, under an Argon atmosphere. 155.7 g of ethanol, 10.41 g of $(CH_3CHCO_2CH_3)S(C=S)OEt$ and 100 g butyl acrylate are introduced in the reactor. The solution obtained is heated at 70° C., and a solution of 3.28 g of azobisisobutyronitrile (AIBN) in 9.85 g of acetone and 4.92 g of ethanol is added. Three hours later, a solution of 1.64 g of AIBN in 4.93 g of acetone and 2.46 g of ethanol is added. A sample is analyzed: the number-average molecular weight measured by GPC-MALLS in dimethylformamide is of 2200 g/mol. A solution of 200 g of 2-dimethylaminoethyl acrylate in 280 g of ethanol is added during three hours. Two hours after the end of the addition a solution of 2.46 g of AIBN in 7.39 g of acetone and 3.69 g of ethanol is added. Two hours later, the same solution is added again. The reaction is continued during two hours and stopped by cooling to room-temperature. The number-average molecular weight if the block copolymer obtained, measured by GPC-MALLS in dimethylformamide, is of 7000 g/mol.

Example 3

The example illustrates the use of the diblock copolymer of example 2 in shampoos compositions.

Emulsion A:

A silicone oil (Rhodorsil 48V5000, Rhodia) is emulsified in mineral-free water (pH 5) with the diblock copolymer of example 2. The emulsion is obtained by:

preparing 27 g of an aqueous solution comprising 0.3 g of the diblock copolymer,
adjusting the pH to 5,
introducing 3 g of the silicone oil,
mixing first with an ultra-turrax at 9500 rpm during 5 minutes, and then with a microfluidizer (5 times, 500 bars).

Shampoo A:

70 g of an aqueous formulation comprising 14 g of sodium laurylethersulfate (Empicol ESB3M), 2 g of tegobetaine T7, and 1.6 g of sodium chloride, is prepared. pH is adjusted to 5.

27 g of emulsion A are added in the 70 g of the formulation, with mixing (300 rpm, 5 minutes).

Emulsion B:

A silicone oil (Rhodorsil 48V5000, Rhodia) is emulsified in mineral-free water (pH 5) with an anionic surfactant (SDS, sodium dodecylsulfate). The emulsion is obtained by:

preparing 27 g of an aqueous solution comprising 0.3 g of the surfactant, adjusting the pH to 5, introducing 3 g of the silicone oil, mixing first with an ultra-turrax at 9500 rpm during 5 minutes, and then with a microfluidizer (5 times, 500 bars).

Shampoo B:

70 g of an aqueous formulation comprising 14 g of sodium laurylethersulfate (Empicol ESB3M), 2 g of tegobetaine T7, and 1.6 g of sodium chloride, is prepared. pH is adjusted to 5. 27 g of emulsion B are added in the 70 g of the formulation, with mixing (300 rpm, 5 minutes).

Dilution of Shampoos A and B:

Shampoos are diluted 10 times in a pH 5 aqueous solution, and the diluted products obtained are inspected with an optical microscope. Diluted shampoo A flocculates whereas shampoo B does not.

Deposition:

Shampoos A and B are used to treat identical hair locks. Silicone deposition after cleaning and rinse-off of the locks by the shampoo is measured by X fluorescence. Deposition higher with shampoo A than with shampoo B.

The invention claimed is:

1. A cosmetic composition comprising a diblock copolymer, comprising two blocks A and B, wherein block A is a polycationic block in the pH conditions of the composition, comprising cationic repetitive units whatever the pH, block B is a neutral block in the pH conditions of the composition, and block A and block B both comprise units deriving from alpha-ethylenically-unsaturated monomers;

further wherein block A comprises repeating units deriving from monomers comprising an ammonium group of formula —$^+NR^3$, wherein R, which is identical or different, represents an alkyl group comprising 1 to 10 carbon atoms, or a benzyl group, optionally carrying a hydroxyl group.

2. A composition according to claim 1, wherein block A comprises repeating units deriving from monomers comprising:

trimethylammonium ethyl (meth)acrylate chloride, trimethylammonium ethyl (meth)acrylate methyl sulphate, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, monomers having the following formula:

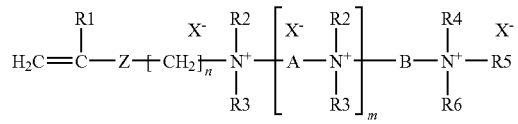

wherein $R_1$ is a hydrogen atom or a methyl or ethyl group; $R_2$, and $R_3$, which are identical or different, are linear or branched $C_1$-$C_6$ alkyl, hydroxyalkyl or aminoalkyl groups;

$R_4$, $R_5$ and $R_6$ which are identical or different are linear or branched $C_1$-$C_6$ alkyl groups;

m is an integer from 1 to 10, for example 1; n is an integer from 1 to 6;

Z represents a —C(O)O— or —C(O)NH— group or an oxygen atom;

A represents a $(CH_2)_p$ group, p being an integer from 1 to 6;

B represents a linear or branched $C_2$-$C_{12}$ polymethylene chain optionally interrupted by one or more heteroatoms or heterogroups and optionally substituted by one or more hydroxyl or amino groups, and X, which are identical or different, represent counterions; or mixtures thereof.

3. A composition according to claim 1, wherein block B comprises repeating units deriving from monomers selected from the group consisting of:

polyethylene and/or polypropylene oxide (meth)acrylates vinyl acetate, amides of alpha-ethylenically-unsaturated carboxylic acids, esters of alpha-ethylenically-unsaturated monocarboxylic acids, vinyl nitriles, vinylamine amides vinyl alcohol vinyl pyrrolidone, and vinyl aromatic compounds.

4. A composition according to claim 1, wherein block B comprises repeating units deriving from monomers selected from the group consisting of:

styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethylhexyl acrylate and 2-hydroxyethylacrylate.

5. A composition according to claim 1, wherein block B is a hydrophilic water-soluble block and comprises units deriving from monomers selected from the group consisting of:

vinyl alcohol, vinyl pyrrolidone, polyethylene oxide (meth)acrylate (i.e. polyethoxylated (meth)acrylic acid), hydroxyalkylesters of alpha-ethylenically-unsaturated, monocarboxylic acids, hydroxyalkylamides of alpha-ethylenically-unsaturated monocarboxylic acids, acrylamide, and methacrylamide.

6. A composition according to claim 1, wherein block B is a hydrophobic block, and comprises units deriving from monomers selected from the group consisting of:

alkylesters of an alpha-ethylenically-unsaturated monocarboxylic acid, acrylonitrile vinyl nitrites, comprising from 3 to 12 carbon atoms, vinylamine amides, and vinylaromatic compounds.

7. A composition according to claim 1, wherein block B is a hydrophobic block, and comprises units deriving from monomers selected from the group consisting of methylacrylate, ethylacrylate, n-propylacrylate, n-butylacrylate, methylmethacrylate, ethylmethacrylate, n-propylmethacrylate, n-butylmethacrylate, and 2-ethyl-hexyl acrylate, and styrene.

8. A composition according to claim 1, wherein the diblock copolymer is obtained by a living or controlled free-radical polymerization process.

9. A composition according to claim 1, comprising ingredients of a composition to be used on skin.

10. A composition according to claim 1, comprising ingredients of a composition to be used on hair.

11. A process for making a cosmetic composition, comprising the step of adding to a cosmetic composition a diblock copolymer, comprising two blocks A and B, wherein block A is a polycationic block in the pH conditions of the composition, comprising cationic repetitive units whatever the pH, block B is a neutral block in the pH conditions of the composition, and block A and block B both comprise units deriving from alpha-ethylenically-unsaturated monomers;

further wherein block A comprises repeating units deriving from monomers comprising an ammonium group of formula $-^+NR^3$, wherein R, which is identical or different, represents an alkyl group comprising 1 to 10 carbon atoms, or a benzyl group, optionally carrying a hydroxyl group.

12. A composition according to claim 6, wherein the vinylaromatic compound is styrene.

13. The composition of claim 2, wherein $R_2$, $R_3$, $R_4$, $R_5$, and $R_6$ comprise $C_1$-$C_4$ alkyl groups.

14. The composition of claim 2, wherein B represents a linear or branched $C_3$-$C_6$, polymethylene chain optionally interrupted by one or more heteroatoms or heterogroups comprising O or NH, and optionally substituted by one or more hydroxyl groups.

* * * * *